United States Patent [19]

Kodaka et al.

[11] Patent Number: 5,192,778
[45] Date of Patent: Mar. 9, 1993

[54] DIALKOXYMETHYLIMIDAZOLIDINE DERIVATIVES, PREPARATION THEREOF, INSECTICIDES CONTAINING SAME AS AN EFFECTIVE INGREDIENT AND INTERMEDIATES THEREFOR

[75] Inventors: Kenji Kodaka; Katsutoshi Kinoshita; Michihiko Nakaya; Koichi Ebihara; Shirou Shiraishi; Eiichi Yamada, all of Mobara; Satoshi Numata, Chiba, all of Japan

[73] Assignee: Mitsui Toatsu Chemicals, Inc., Tokyo, Japan

[21] Appl. No.: 677,030

[22] Filed: Mar. 29, 1991

[30] Foreign Application Priority Data

Apr. 3, 1990 [JP] Japan .................................... 2-87368
Feb. 26, 1991 [JP] Japan .................................... 3-30815

[51] Int. Cl.$^5$ .................... C07D 401/06; A61K 31/44
[52] U.S. Cl. .................................... 514/341; 514/365; 514/256; 546/278; 548/205; 548/311.1; 548/322.5; 544/330; 544/331
[58] Field of Search .................. 546/278; 548/205; 514/365, 341

[56] References Cited

U.S. PATENT DOCUMENTS 4,588,736 5/1986 Esser et al. .................... 548/316
4,742,060 5/1988 Shiokawa ......................... 514/252

FOREIGN PATENT DOCUMENTS 0277317 8/1988 European Pat. Off. .
0285985 10/1988 European Pat. Off. .
0315826 5/1989 European Pat. Off. .

Primary Examiner—Jane T. Fan
Attorney, Agent, or Firm—Millen, White, Zelano and Branigan

[57] ABSTRACT

Novel dialkoxymethylimidazolidine derivatives of the formula (1)

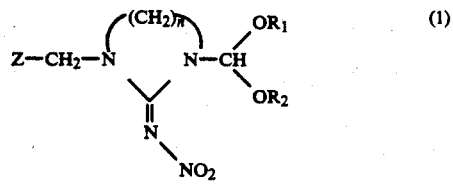

are described. Also, a preparation process of the derivatives and insecticidal compositions comprising the same are set forth. In addition, novel intermediate compounds of the formula (2) useful in preparing the derivatives of the formula(1) are also described along with their preparation process

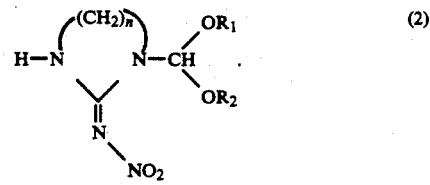

4 Claims, No Drawings

DIALKOXYMETHYLIMIDAZOLIDINE DERIVATIVES, PREPARATION THEREOF, INSECTICIDES CONTAINING SAME AS AN EFFECTIVE INGREDIENT AND INTERMEDIATES THEREFOR

BACKGROUND OF THE INVENTION

1. Field of the Invention

This invention relates to novel imidazolidine derivatives, their preparation, insecticides containing the derivatives as an effective ingredient, novel intermediates and their preparation. More particularly, the invention relates to imidazolidine derivatives of the formula (1), a preparation process thereof, and insecticides containing the derivatives as an effective ingredient

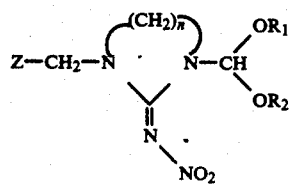

and also to intermediate compounds of the formula (2), and a preparation process thereof

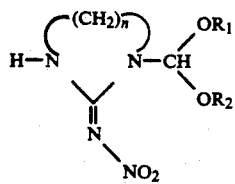

The imidazolidine derivatives (1) of the invention are useful as an agricultural chemical (particularly, as an insecticide) in the fields of agriculture and the imidazolidine derivatives (2) are useful in various industrial fields and particularly as intermediates for agricultural chemicals.

2. Description of the Prior Art

A great number of insecticidally active compounds having the same skelton as the compounds of the invention represented by the formula (1) are known in the art (Japanese Laid-open Patent Application Nos. 62-81382 and 63-156786, and the like).

There are also known a number of compounds having the same skelton as the intermediate for the compounds (1) of the invention represented by the formula (2) (Japanese Laid-open Patent Application No. 63-156786 and the like).

SUMMARY OF THE INVENTION

It is an object of the present invention to provide novel imidazolidine derivatives having good insecticidal activity and a simple process for preparing the derivatives.

It is another object of the invention to provide insecticides of high activity containing the derivatives as an effective ingredient.

It is a further object of the invention to provide a novel intermediate compounds for the imidazolidine derivatives.

According to the invention, there is provided a novel imidazolidine derivative of the formula (1)

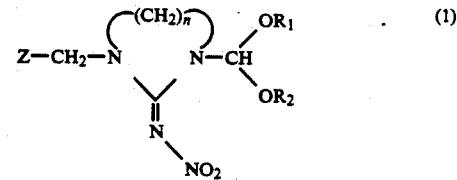

wherein Z represents a 2-chloropyridin-5-yl group or a 2-chlorothiazol-5-yl group, $R_1$ and $R_2$ independently represent a lower alkyl group having from 1 to 6 carbon atoms, a lower haloalkyl group having from 1 to 3 carbon atoms or a lower alkyl group having from 1 to 3 carbon atoms and substituted with a lower alkoxy group having from 1 to 3 carbon atoms provided that $R_1$ and $R_2$ may be joined to form a cyclic alkylene group having from 2 to 3 carbon atoms, and n is a value of 2 or 3. The preparation of the imidazolidine derivative of the formula (1) and insecticides containing the derivative as an effective ingredient are also provided according to the invention.

Moreover, there are also provided an intermediate of the following formula (2) used to prepare the derivative of the formula (1), and its preparation,

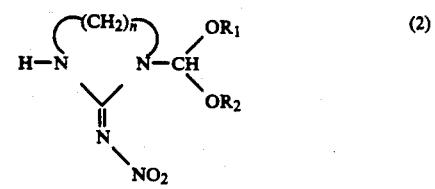

wherein $R_1$ and $R_2$ independently represent a lower alkyl group having from 1 to 6 carbon atoms, a lower haloalkyl group having from 1 to 3 carbon atoms or a lower alkyl group having from 1 to 3 carbon atoms and substituted with a lower alkoxy group having from 1 to 3 carbon atoms provided that $R_1$ and $R_2$ may be joined to form a cyclic alkylene group having from 2 to 3 carbon atoms as defined in the formula (1), and n is a value of 2 or 3.

DETAILED DESCRIPTION AND EMBODIMENTS OF THE INVENTION

In the formula (1) set forth above, Z is a 2-chloropyridin-5-yl group or a 2-chlorothiazol-5-yl group. In the formulae (1) and (2), the lower alkyl group represented by $R_1$ and $R_2$ has from 1 to 6 carbon atoms, typical of which is a methyl group, an ethyl group, a n-propyl group, an iso-propyl group, a n-butyl group, an i-butyl group, a sec-butyl group, a n-pentyl group, a n-hexyl group or the like. The $R_1$ and $R_2$ may be joined to represent a cyclic alkylene group. Examples of the cyclic alkylene group include a dimethylene group, a trimethylene group or the like. Typical examples of the haloalkyl group having from 1 to 3 carbon atoms include a 2-bromoethyl group, a 2-chloroethyl group, a 2,2,2-trichloroethyl group, a 2-fluoroethyl group, a 2,2-difluoroethyl group, a 2,2,2-trifluoroethyl group and the like. Typical examples of the lower alkyl group having from 1 to 3 carbon atoms and substituted with a lower alkoxy group having from 1 to 3 carbon atoms include a 2-methoxyethyl group, a 2-ethoxyethyl group, a 2-isopropoxyethyl group, a 1-methoxymethyl-ethyl group and the like.

The compounds of the formula (1) can be prepared according to the following procedure.

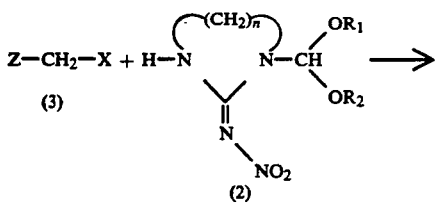

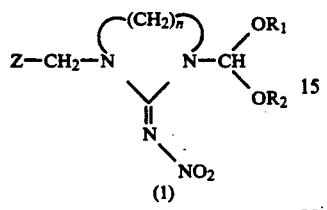

wherein Z represents a 2-chloropyridin-5-yl group or a 2-chlorothiazol-5-yl group as defined before, $R_1$ and $R_2$ have, respectively, the same meanings as defined above and thus independently represent a lower alkyl group having from 1 to 6 carbon atoms, a lower haloalkyl group having from 1 to 3 carbon atoms or a lower alkyl group having from 1 to 3 carbon atoms and substituted with a lower alkoxy group having from 1 to 3 carbon atoms provided that $R_1$ and $R_2$ may be joined to form a cyclic alkylene group having from 2 to 3 carbon atoms, n is a value of 2 or 3, and X represents a chlorine atom or a bromine atom.

More particularly, the compound of the formula (2) and 2-chloro-5-halomethylpyridine or 2-chloro-5-halomethylthiazole of the formula (3) are reacted in the presence of a deacidifying agent in various solvents to readily prepare the compounds of the formula (1).

Examples of the deacidifying agent include alkali metal hydroxides such as sodium hydroxide, potassium hydroxide and the like alkaline earth metal hydroxides such as magnesium hydroxide, calcium hydroxide and the like, alkali metal hydrides such as sodium hydride, potassium hydride, alkali metal alcoholates such as sodium methylate, sodium ethylate and the like, alkali metal oxides such as sodium oxide, alkali metal carbonates such as sodium carbonate, potassium carbonate and the like, alkali metal sodium hydrogencarbonates such as sodium hydrogencarbonate, potassium hydrogencarbonate and the like, hydrogensulfates such as sodium hydrogensulfate, potassium hydrogensulfate and the like, phosphates, trisodium phosphate, disodium phosphate and the like, acetates such as sodium acetate, potassium acetate and the like, organic salts such as triethylamine, DBU, DIMAP and the like, butyl lithium, sodium amide, and the like.

The solvents may include not only water, aromatic hydrocarbons such as benzene, toluene, xylene and the like, aliphatic hydrocarbons such as hexane, heptane, petroleum benzene and the like, aprotic non-polar solvents such as dimethylformamide, dimethylacetamide, dimethylsulfoxide, 1,3-dimethyl-2-imidazolidinone, 1-methyl-2-pyrrolidinone and the like, ethers such as ethyl ether, diisopropyl ether, 1,2-dimethoxyethane, tetrahydrofuran, dioxane and the like, nitriles such as acetonitrile, propionitrile and the like, and ketones such as acetone, diisopropyl ketone and the like.

When there are used phase transfer catalysts such as tetrabutylammonium bromide, triethylbenzylammonium chloride and the like, intended imidazolidine derivatives (1) can be obtained in high yield.

The reaction temperature and the reaction time can be varied over wide ranges. In general, the reaction temperature is in the range of $-20°$ to $200°$ C., preferably from $0°$ to $100°$ C. and the reaction time is in the range of from 0.01 to 30 hours, preferably from 0.1 to 15 hours.

The compounds (1) of the invention may include isomers of the following formula.

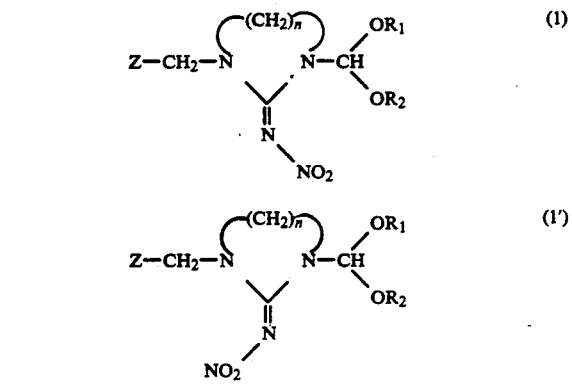

In the above reaction formula, the starting material of the formula (2) can be prepared according to the following reaction sequence

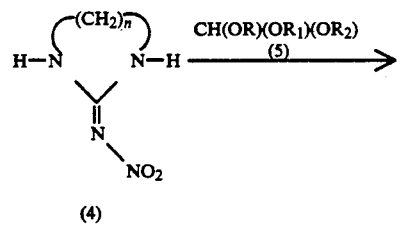

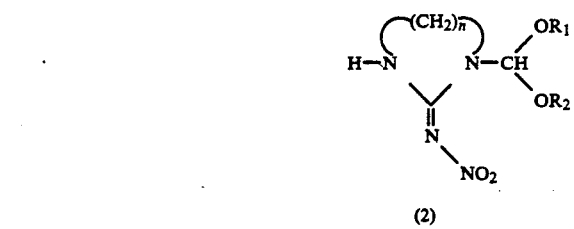

wherein R represents a lower alkyl group having from 1 to 6 carbon atoms, a lower haloalkyl group having from 1 to 3 carbon atoms, a lower alkyl group having from 1 to 3 carbon atoms and substituted with a lower alkoxy group having from 1 to 3 carbon atoms, $R_1$ and $R_2$ independently represent a lower alkyl group having from 1 to 6 carbon atoms, a lower haloalkyl group having from 1 to 3 carbon atoms, or a lower alkyl group having from 1 to 3 carbon atoms and substituted with a lower alkoxy group having from 1 to 3 carbon atoms, or $R_1$ and $R_2$ may be joined to complete an alkylene group having from 2 to 3.

More particularly, the compounds (1) can be readily prepared in high yield by reaction between the nitroguanidine derivative of the formula (4) (literature on its preparation: J. Am. Chem. Soc., 70, 430 (1948)) and an orthoformic acid ester derivative (literature on its preparation: Synthesis, 153(1974)). The compound represented by the formula (2) is a novel compound which was synthesized by us for the first time and its synthetic reaction is a novel reaction which we first found.

The reaction is feasible in the absence of or in solvents. Examples of the solvent include aromatic hydrocarbons such as benzene, toluene, xylene and the like, halogenated hydrocarbons such as chloroform, 1,2-dichloroethane and the like, ethers such as diisopropyl ether, 1,2-dimethoxyethane, tetrahydrofuran, dioxane and the like, aprotic polar solvents such as dimethylformamide, dimethylsulfoxide, sulforan, 1,3-dimethyl-2-imidazolidinone and the like, nitriles such as acetonitrile, propionitrile and the like, and ketones such as acetone, methyl isobutyl ketone and the like.

The reaction temperature and the reaction time can be widely varied. In general, the reaction temperature is in the range of from 50° to 300° C., preferably from 70° to 200° C. The reaction is usually carried out under normal pressure conditions and may be likewise performed under pressure.

Although not necessarily required, catalysts may be used including mineral acids such as sulfuric acid, hydrochloric acid, phosphoric acid, nitric acid and the like, sulfonic acids such as p-toluenesulfonic acid, methanesulfonic acid, trifluoromethanesulfonic acid and the like, carboxylic acids such as formic acid, acetic acid, benzoic acid and the like, Lewis acids such as aluminum chloride, tin tetrachloride, zinc chloride, boron trifluoride, titanium tetrachloride and the like, pyridine hydrochloric acid salt, ammonium salts such as tetrabutylammonium chloride, and acidic or basic oxides such as zirconium oxide, silica gel, alumina and the like.

The reaction time is in the range of from 0.1 to 30 hours, preferably from 0.5 to 20 hours.

The amount of the orthoformic acid ester derivative (5) may be not less than 1.0 mole per mole of the nitroguanidine derivative (4) and is preferably in the range of from 1.0 to 10.0 moles in view of the economy.

This reaction is usually effected under normal pressure conditions and may be likewise performed under pressure.

The compound (2) of the invention may include E and Z isomers along with a tautomer as shown below

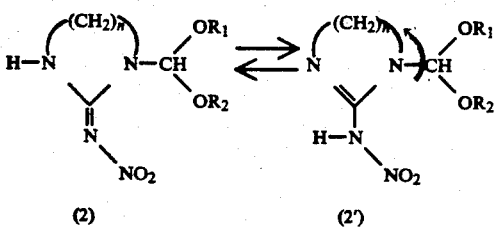

(2)      (2')

On the other hand, the chloropyridylmethyl halides of the formula (3) are known compounds and can be prepared according to a procedure described in literature (literature on the preparation: J. Heterocyclic Chem., 16, 333 (1979) and J. Med. Chem., 14, 557 (1971)). The thiazolylmethyl halides can be obtained by subjecting 2-amino-5-alkoxycarbonylthiazoles to diazotization, introducing halogen atoms, reducing the halogenated products with a lithium aluminium halide by a usual manner, and subjecting the resulting 2-halogeno-5-hydroxymethylthiazoles to conversion with halogen atoms by a usual manner.

The derivatives of the formula (1) according to the invention have great insecticidal activity and can be used as an insecticide. The derivatives of the formula (1) of the invention show a high control effect on harmful insects without involving any phyto-toxicity to cultivated plants.

Insect pests to which the derivatives of the invention can be applied, for instance, include:

Lepidoptera

*Pieris rapae crucivora* Boisduval—Common cabbageworm
*Spodoptera litura* Fabricius—Common cutworm
*Ostrinia furnacalis* Guenee—Oriental corn borer
*Plutella xylostella* Linne—Diamond backmoth
*Chilo supprossalis* Walker—Rice stem borer

Hemiptera

*Nephotettix cincticeps* Uhler—Green rice leafhopper
*Nilaparvata lugens* Stal—Brown rice planthopper
*Laodelphax striatellus* Fallen—Small brown planthopper
*Unaspis yanonensis* Kuwana—Arrowhead scale
*Myzus persicae* Sulzer—Green peach aphid
*Aphis gossypii* Glover—Cotton aphid
*Lipaphis pseudobrassicae* Davis—Turnip aphid
*Nezara antennata* Scott—Common green stink bug
*Trialeurodes vaporariorum* Westwood—Greenhouse whitefly

Coleoptera

*Callosobruchus chinensis* Linne—Azuki bean weevil
*Sitophilus oryzae* Linne—Rice Weevil
*Henosepilachna vigintioctopunctata* Fablicius—28-spotted lady bettle
*Anomala rufocuprea* Motschulsky—Soy bean beetle
*Leptinotarsa decemlineata* Say—Colorado potato beetle
*Lissorhoptrus oryzophilus* Kuschel—Rice water weavil

Orthoptera

*Blattella germanica* Linne—German cockroach
*Periplaneta americana* Linne—American cockroach
*Gryllotalpa africana* palisot de Beauvois—African mole cricket
*Locusta migratoria* danica Linne—Asiatic locust
*Reticulitermes speratus* kolbe
*Coptatermes formosanus* Shiraki—Formosan subleronean termite

Diptera

*Musca domestica* vicina Macuart—House fly
*Aedes aegypti* Linne—Yellow fever mosquito
*Culex pipiens* pallens—Coquillett
*Culex tritaeniorhyneus*—Giles Where the compounds of the formula (1) of the invention is actually applied, it may be used singly without addition of any other ingredient. However, it is usual to formulate carriers in order to make easy application as a control chemical.

For preparation of the compounds of the invention, any specific requirement is not necessary and optional preparations, such as emulsions, dusts, granules, fine powders, oils, aerosols, poisonous feeds and the like, according to the procedures of preparing general agricultural chemicals well known in the art.

The term "carrier" used herein is intended to mean synthetic or natural, organic or inorganic materials which assist the effective ingredient to arrive at sites or portions to be treated and which are formulated in order to make easy storage, transport and handling of the effective compound. Appropriate solid carriers include, for example, clays such as montomorillonite, kaolinite and the like, inorganic substances such as diatomaceous earth, white clay, talc, vermiculite, gypsum, calcium carbonate, silica gel, ammonium sulfate and the like, plant organic substances such as soybean flour, saw dust, wheat flour and the like, and urea.

Suitable liquid carriers include, for example, aromatic hydrocarbons such as toluene, xylene, cumene and the like, paraffin hydrocarbons such as kerosine, mineral oils and the like, halogenated hydrocarbons such as carbon tetrachloride, chloroform, dichloroethane and the like, ketones such as acetone, methyl ethyl ketone and the like, ethers such as dioxane, tetrahydrofuran and the like, alcohols such as methanol, ethanol, propanol, ethylene glycol and the like, dimethylformamide, dimethyl sulfoxide, water and the like.

In order to reinforce the efficacy of the compound of the formula (1) of the invention, the following adjuvants may be used singly or in combination, depending on the type of preparation, the manner of application and the purpose.

For the purposes of emulsification, dispersion, spreading, wetting, bonding and stabilization, there are used water-soluble salts such as ligninsulfonates, nonionic surface active agents such as alkylbenzene sulfonates, alkylsulfates and the like, lubricants such as calcium stearate, waxes and the like, stabilizers such as isopropoxyhydrogenphosphates, and methyl cellulose, carboxymethyl cellulose, casein, gun arabic and the like. It should be noted that the adjuvants are not limited to those mentioned above and other adjuvants ordinarily used for this purpose may also be used.

The compounds of the formula (1) of the invention may develop better insecticidal activity when used in combination of two or more. If other physiologically active substances or chemicals are used in combination, multi-purpose compositions with good efficacy can be prepared with the possibility of developing a synergistic effect. Examples of such physiologically active substances include: synthetic pyrethroids, and isomers thereof or pyrethrum extracts, such as allethrin, N-(chrysanthemoylmethyl)-3,4,5,6-tetrahydrophthalimide, 5-benzyl-3-furylmethyl chrysanthemate, 3-phenoxybenzyl chrysanthemate, 5-propargylfurfuryl chrysanthemate and other known cyclopropanecarboxylic acid esters, 3-phenoxybenzyl 2,2-dimethyl-3-(2,2-dichlorovinyl)-cyclopropane-1-carboxylate, 2,2-dimethyl-3-(2,2-dibromovinyl)-cyclopropane-1-carboxylate, 3-phenoxy-α-cyanobenzyl α-isopropyl-4-chlorophenylacetate and the like; organophosphate insecticides such as O,O-diethyl-O-(3-oxo-2-phenyl-2H-pyridazin-6-yl)phosphorothioate (available from Mitsui-Toatsu Chem. Ind. Co., Ltd. under the trade name of Ofunack), O,O-dimethyl-O-(2,2-dichlorovinyl)-phosphate (DDVP), O,O-dimethyl-O-(3-methyl-4-nitrophenyl)phosphorothioate, diazinon, O,O-dimethyl-O-4-cyanophenylphosphorothioate, O,O-dimethyl-S-[α-(ethoxycarbonyl)benzyl]phosphorodithioate, 2-methoxy-4H-1,3,2-benzodioxaphosphorin-2-sulfide, O-ethyl-O-4-cyanophenylphosphonothioate and the like; carbamate insecticides such as 1-naphthyl N-methylcarbamate (NAC), m-tolyl N-methylcarbamate (MTMC), 2-dimethylamino-5,6-dimethylpyrimidin-4-yl dimethylcarbamate (Pyrimer), 3,4-dimethylphenyl N-methylcarbamate, 2-isopropoxyphenyl N-methylcarbamate and the like; aryl propyl ether insecticides such as 3-phenoxybenzyl 2-(4-chlorophenyl)-2-methyl propyl ether, 3-phenoxy-4-fluorobenzyl 2-(4-chlorophenyl)-2-methylpropyl ether, 3-phenoxybenzyl 2-(4-ethoxyphenyl)-2-methylpropyl ether, 3-phenoxy-4-(fluorobenzyl 2-(4-ethoxyphenyl)-2-methylpropyl ether and the like; aromatic alkane insecticides such as 1-(3-phenoxyphenyl)-4-(4-chlorophenyl)-4-methylpentane, 1-(3-phenoxy-4-fluorophenyl)-4-(4-chlorophenyl)-4-methylpentane, 1-(3-phenoxyphenyl)-4-(4-ethoxyphenyl)-4-methylpentane, 1-(3-phenoxy-4-fluorophenyl)-4-(4-ethoxyphenyl)-4-methylpentane and the like; and other insecticides, acaricides, fungicides, nematicides, herbicides, plant growth regulators, fertilizes, BT agents, insect hormone compounds, and other agricultural chemicals.

Although the compounds of the formula (1) of the invention are stable against light, heat and oxidation, antioxidants or UV absorbers may be added in appropriate amounts, if necessary, including, for example, phenol derivatives or bisphenol derivatives such as BHT (2,6-di-t-butyl-4-methylphenol), BHA (butylhydroxyanisole) and the like, arylamines or benzophenone compounds such as phenyl-α-naphtylamine, phenyl-β-naphthylamine, a condensate of phenetidine and acetone, thereby obtaining more stable compositions.

When the compounds of the formula (1) of the invention are used as an insecticide, they are used in an amount of from 0.0001 to 95 wt %, preferably from 0.01 to 50 wt % of the insecticide.

When the insecticide of the invention is applied, the effective ingredient is used at a concentration of 0.01 to 5000 ppm, preferably from 0.1 to 1000 ppm.

The application amount per 10 acres is generally in the range of from 1 to 300 g of the effective ingredient.

The present invention is more particularly described by way of examples, which should not be construed as limiting the invention.

SYNTHESIS EXAMPLE 1 (COMPOUND NO. 1)

17.6 g of 1-diethoxymethyl-2-nitroiminoimidazolidine and 21.0 g of anhydrous potassium carbonate were added to 200 ml of dimethylformamide. While agitating at 70° C., a solution of 12.3 g of 2-chloro-5-chloromethylpyridine in 30 ml of dimethylformamide was dropped in the mixture.

After completion of the dropping, the reaction mixture was poured into water, followed by extraction with ethyl acetate. After washing with water, the extract was dried with anhydrous magnesium sulfate and the solvent was distilled off under reduced pressure to give 25.0 g of an oily residue. This was purified by column chromatography [silica gel, eluant: hexane/ethyl acetate (1:2)] to obtain 11.3 g of 1-diethoxymethyl-2-nitroimino-3-(2-chloropyridin-5-ylmethyl)imidazolidine.

SYNTHESIS EXAMPLE 2 (COMPOUND NO. 3)

15.0 g of 1-(1-ethoxy-1-propoxy)methyl-2-nitroiminoimidazolidine, 11.6 g of anhydrous potassium carbonate, 11.3 g of 2-chloro-5-chloromethylpyridine and 60 ml of dimethyl sulfoxide were agitated at 75° C. for 1 hour. The reaction mixture was poured into water, and extracted with ethyl acetate. After washing with water, the extract was dried with anhydrous sodium sulfate, after which the solvent was distilled off under reduced pressure. The resultant oily residue was purified by column chromatography [silica gel, eluant: hexane/ethyl acetate (1:2)] to give 4.7 g of 1-(1-ethoxy-1-propoxy)methyl-2-nitroimino-3-(2-chloropyridin-5-ylmethyl)imidazolidine.

SYNTHESIS EXAMPLE 3 (COMPOUND NO. 5)

6.8 g of 1-[1-ethoxy-1-(2-methoxyethoxy)]methyl-2-nitroiminoimidazolidine, 4.8 g of anhydrous potassium carbonate, 6.0 g of 2-chloro-5-chloromethylpyridine and 20 ml of dimethyl sulfoxide were agitated at 70° C. for 1 hour.

The reaction mixture was poured into water, and extracted with ethyl acetate. After washing with water, the extract was dried with anhydrous sodium sulfate, after which the solvent was distilled off under reduced pressure. The resultant oily residue was purified by column chromatography [silica gel, eluant: hexane/ethyl acetate (1:2)] to give 2.8 g of 1-[1-ethoxy-1-(2-methoxyethoxy)]methyl-2-nitroimino-3-(2-chloropyridin-5-ylmethyl)imidazolidine.

SYNTHESIS EXAMPLE 4 (COMPOUND NO. 6)

16.0 g of 1-[bis-(2-chloroethoxy)methyl]-2-nitroiminoimidazolidine, 13.0 g of anhydrous potassium carbonate, 13.0 g of 2-chloro-5-chloromethylpyridine and 70 ml of dimethyl sulfoxide were agitated at 70° C. for 1 hour. The reaction mixture was poured into water, and extracted with ethyl acetate. After washing with water, the extract was dried with anhydrous sodium sulfate, after which the solvent was distilled off under reduced pressure. The resultant oily residue was purified by column chromatography [silica gel, eluant: hexane/ethyl acetate (1:2)] to give 14.0 g of 1-[bis-(2-chloroethoxy)-methyl]-2-nitroimino-3-(2-chloropyridin-5-ylmethyl)imidazolidine.

SYNTHESIS EXAMPLE 5 (COMPOUND NO. 7)

7.0 g of 1-[1-ethoxy-1-(2,2,2-trifluoroethoxy)]methyl-2-nitroiminoimidazolidine, 7.0 g of anhydrous potassium carbonate, 7.0 g of 2-chloro-5-chloromethylpyridine and 45 ml of dimethyl sulfoxide were agitated at 70° C. for 1 hour.

The reaction mixture was poured into water, and extracted with ethyl acetate. After washing with water, the extract was dried with anhydrous sodium sulfate, after which the solvent was distilled off under reduced pressure. The resultant oily residue was purified by column chromatography [silica gel, eluant: hexane/ethyl acetate (1:2)] to give 2.3 g of 1-[1-ethoxy-1-(2,2,2-trifluoroethoxy)]methyl-2nitroimino-3-(2-chloropyridin-5-ylmethyl)imidazolidine.

SYNTHESIS EXAMPLE 6 (COMPOUND NO. 9)

6.0 g of 1-dimethoxymethyl-2-nitroiminoimidazolidine and 8.6 g of anhydrous potassium carbonate were added to 50 ml of dimethyl sulfoxide. While agitating at 70° C., a solution of 5.5 g of 2-chloro-5-chloromethyl-pyridine in 10 ml of dimethyl sulfoxide was dropped in the mixture in 20 minutes, followed by further agitation at the same temperature for 30 minutes.

After completion of the dropping, the reaction mixture was poured into water, and extracted with ethyl acetate. After washing with water, the extract was dried with anhydrous magnesium sulfate and the solvent was distilled off under reduced pressure to give 13.7 g of an oily residue. The residue was purified by column chromatography [silica gel, eluant: hexane/ethyl acetate (1:2)] to give 4.8 g of 1-dimethoxymethyl-2-nitroimino-3-(2-chloropyridin-5-ylmethyl)imidazolidine.

SYNTHESIS EXAMPLE 7 (COMPOUND NO. 10)

5.5 g of 1-diethoxymethyl-2-nitroiminohexahydropyrimidine and 6.5 g of anhydrous potassium carbonate were added to 50 ml of dimethylformamide. While agitating at 70° C., a solution of 3.8 g of 2-chloro-5-chloromethylpyridine in 10 ml of dimethylformamide was dropped in the mixture, followed by further agitation at the same temperature for 40 minutes.

After completion of the dropping, the reaction mixture was poured into water, and extracted with ethyl acetate. After washing with water, the extract was dried with anhydrous magnesium sulfate and the solvent was distilled off under reduced pressure to give 11.0 g of an oily residue. The residue was purified by column chromatography [silica gel, eluant: hexane/ethyl acetate (1:2)] to give 2.3 g of 1-diethoxymethyl-2-nitroimino-3-(2-chloropyridin-5-ylmethyl)hexahydropyrimidine.

SYNTHESIS EXAMPLE 8 (COMPOUND NO. 11)

5.0 g of 1-diethoxymethyl-2-nitroiminoimidazolidine and 6.0 g of anhydrous potassium carbonate were added to 50 ml of dimethyl sulfoxide. While agitating at 70° C., a solution of 3.9 g of 2-chloro-5-chloromethylthiazole in 5 ml of dimethyl sulfoxide was dropped in the mixture, followed by further agitation at the same temperature for 1.5 hours.

After completion of the dropping, the reaction mixture was poured into water, and extracted with ethyl acetate. After washing with water, the extract was dried with anhydrous magnesium sulfate and the solvent was distilled off under reduced pressure to give 9.8 g of an oily residue. The residue was purified by column chromatography [silica gel, eluant: hexane/ethyl acetate (1:2)] to give 5.4 g of 1-diethoxymethyl-2-nitroimino-3-(2-chlorothiazol-5-ylmethyl)imidazolidine.

Typical compounds of the formula (1) which were prepared according to procedures similar to those described in Examples 1 to 8 are shown in Tables 1 and 2.

TABLE 1

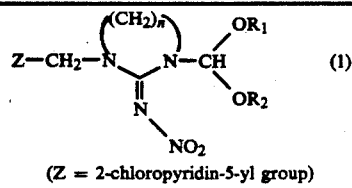

(Z = 2-chloropyridin-5-yl group)

| Compound No. | Substituents $R_1$ | $R_2$ | n | Values of Physical Properties |
|---|---|---|---|---|
| 1 | Et | Et | 2 | δTMS (CDCl$_3$) (ppm): 1.25(6H, t, J=6.9Hz), 3.52~3.82(8H, m), |

TABLE 1-continued

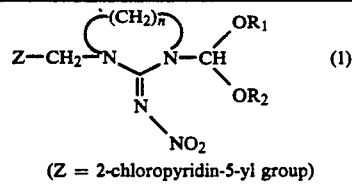

(Z = 2-chloropyridin-5-yl group)

| Compound No. | Substituents R₁ | R₂ | n | Values of Physical Properties |
|---|---|---|---|---|
| | | | | 4.48(2H, s), 5.76(1H, s), 7.37(1H, d, JAB=8.4Hz), 7.72(1H, dd, JAB=8.4Hz, J=2.5Hz), 8.32(1H, d, J=2.5Hz)<br>νMAX (KBr) (cm⁻¹): 1560, 1520, 1460, 1425, 1250, 1100, 1050<br>Elementary Analysis ($C_{14}H_{20}ClN_5O_4$):<br>　　　　　　　　　C　　H　　Cl　　N<br>Calculated (%)　47.00　5.63　9.91　19.57<br>Found (%)　　　47.52　5.61　9.72　20.22<br>m.p.: 87.0~87.5° C. |
| 2 | n-Pr | n-Pr | 2 | δTMS (acetone-d₆) (ppm): 0.92~0.99(6H, m), 1.57~1.67(4H, m), 3.44~3.51(2H, m), 3.53~3.61(4H, m), 3.76~3.84(2H, m), 4.48(2H, s), 5.75(1H, s), 7.36(1H, d, J=8.1Hz), 7.72(1H, dd, J=8.1Hz, J=2.2Hz), 8.33(1H, d, J=2.2Hz)<br>νMAX (neat) (cm⁻¹): 1552, 1462, 1255, 1101 |
| 3 | nPr | Et | 2 | δTMS (acetone-d₆) (ppm): 0.92~0.99(3H, m), 1.21~1.28(3H, m), 1.57~1.69(2H, m), 3.44~3.61(6H, m), 3.74~3.84(2H, m), 4.54(2H, s), 5.75(1H, s), 7.34~7.38(1H, m), 7.69~7.73(1H, m), 8.32(1H, s)<br>νMAX (neat) (cm⁻¹): 1557, 1455, 1100 |
| 4 | iso-Pr | iso-Pr | 2 | δTMS (acetone-d₆) (ppm): 1.15~1.20(12H, m), 3.78~3.93(6H, m), 4.55(2H, s), 5.86(1H, s), 7.47(1H, d, J=8.8Hz), 7.85(1H, dd, J=8.8Hz, J=2.2Hz), 8.40(1H, d, J=2.2Hz)<br>νMAX (KBr) (cm⁻¹): 1564, 1255, 1100<br>m.p.: 78~79° C. |
| 5 | CH₃OC₂H₄ | Et | 2 | δTMS (acetone-d₆) (ppm): 1.19(3H, t, J=7, 3Hz), 3.30(3H, s), 3.51~3.82(10H, m), 4.55(2H, s), 5.79(1H, s), 7.47(1H, d, J=8.1Hz), 7.86(1H, dd, J=8.1Hz, J=2.2Hz), 8.42(1H, d, J=2.2Hz)<br>νMAX (neat) (cm⁻¹): 1553, 1461, 1257, 1106 |
| 6 | ClC₂H₄ | ClC₂H₄ | 2 | δTMS (acetone-d₆) (ppm): 3.75~4.00(12H, m), 4.57(2H, s), 5.92(1H, s), 7.46(1H, d, J=7.1Hz), 7.85(1H, dd, J=7.1Hz, J=2.2Hz), 8.41(1H, d, J=2.2Hz)<br>νMAX (neat) (cm⁻¹): 1558, 1463, 1255, 1106 |
| 7 | CF₃CH₂ | Et | 2 | δTMS (acetone-d₆) (ppm): 1.23(3H, m), 3.6~3.77(2H, m), 3.83~3.87(4H, m), 4.21(2H, q, J=8.8Hz), 4.57(2H, s), 5.94(1H, s), 7.47(1H, d, J=8.1Hz), 7.86(1H, dd, J=8.1Hz, J=2.2Hz), 8.42(1H, d, J=2.2Hz)<br>νMAX (neat) (cm⁻¹): 1558, 1455, 1277, 1104 |
| 8 | CF₃CH₂ | Me | 2 | δTMS (acetone-d₆) (ppm): 3.42(3H, s), 3.6~4.00(4H, m), 4.16(2H, q, J=13.5Hz), 4.53(2H, s), 5.81(1H, s), 7.37(1H, d, J=8.1Hz), 7.67~7.90(1H, m), 8.30~8.43(1H, m)<br>νMAX (neat) (cm⁻¹): 1558, 1455, 1278, 1109 |
| 9 | Me | Me | 2 | δTMS (acetone-d₆) (ppm): 3.37(6H, s), 3.7~3.85(4H, m), 4.56(2H, s), 5.56(1H, s), 7.48(1H, d, J=8.1Hz), 7.87(1H, dd, J=8.1Hz, J=2.2Hz), 8.43(1H, d, J=2.2Hz)<br>νMAX (KBr) (cm⁻¹): 1561, 1535, 1447, 1282, 1099<br>m.p.: 62.0~64.0° C. |
| 10 | Et | Et | 3 | δTMS (CDCl₃) (ppm): 1.24(6H, t, J=7.3Hz), 2.01~2.06(2H, m), 3, 33(2H, t, J=5.9Hz), 3.52(2H, t, J=5.9Hz), 3.55~3.62(2H, m), 3.66~3.73(2H, m), 4.61(2H, s), 6.09(1H, s), 7.37(1H, d, J=8.3Hz), 7.76(1H, dd, J=8.3Hz, J=2.4Hz), 8.33(1H, d, J=2.2Hz)<br>νMAX (neat) (cm⁻¹): 1589, 1502, 1408, 1290, 1101<br>n_D: 1.5486(20° C.) |

TABLE 2

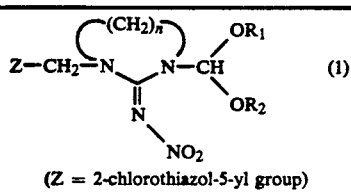

(Z = 2-chlorothiazol-5-yl group)

| Compound No. | Substituents R₁ R₂ | n | Values of Physical Properties |
|---|---|---|---|
| 11 | Et Et | 2 | δTMS (DMSO-d₆) (ppm): 1.14(6H, t, J=7.3Hz), 3.47~3.61(4H, m), 3.63~3.71(4H, m), 4.52(2H, s), 5.65(1H, s), 7.68(1H, s) |

TABLE 2-continued

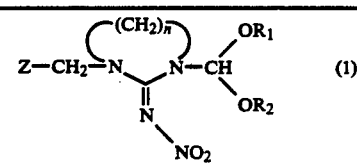

(Z = 2-chlorothiazol-5-yl group)

| Compound No. | Substituents R₁ R₂ | n | Values of Physical Properties |
|---|---|---|---|
| | | | 3.71(4H, m), 4.52(2H, s), 5.65(1H, s), 7.68(1H, s) |

TABLE 2-continued $$Z-CH_2-N \overset{(CH_2)_{\overline{n}}}{\underset{\underset{NO_2}{\overset{\|}{N}}}{\diagdown}} N-CH \overset{OR_1}{\diagdown} \quad (1)$$

(Z = 2-chlorothiazol-5-yl group)

| Compound No. | Substituents R₁ | R₂ | n | Values of Physical Properties |
|---|---|---|---|---|
| | | | | νMAX (neat) (cm⁻¹): 1528, 1419, 1255, 1100 |

Then, preparation of intermediate compounds of the general formula (2) is described.

SYNTHESIS EXAMPLE 9 (Intermediate No. 1)

A mixture of 25 g of 2-nitroiminoimidazolidine, 100 g of ethyl orthoformate and 25 ml of 1,3-dimethyl-2-imidazolidinone was heated under reflux for 3 hours. After cooling to room temperature, the mixture was poured into water, followed by extraction with ethyl acetate. After washing with water, the extract was dried with anhydrous magnesium sulfate, after which the solvent was distilled off under reduced pressure. The resultant crystals were sludged with ether to give 32 g of 1-diethoxymethyl-2-nitroiminoimidazolidine.

SYNTHESIS EXAMPLE 10 (Intermediate No. 5)

16.5 g of 2-nitroiminoimidazolidine and 18.0 g of ethylenedioxymethyl ethyl ether were heated under reflux for about 4 hours while removing the resultant distillate by means of the Dean-Stark trap. After cooling to room temperature, the reaction mixture was purified by column chromatography [silica gel, eluant: hexane/ethyl acetate (1:2)] to give 1.9 g of ethylenedioxymethyl-2-nitroimioimidazolidine.

SYNTHESIS EXAMPLE 11 (Intermediate No. 6)

9.9 g of 2-nitroiminoimidazolidine and 18.0 g of n-propyl orthoformate were heated under reflux for about 4 hours while removing a distillate by means of Dean-Stark trap. After cooling to room temperature, the reaction mixture was purified by column chromatography [silica gel, eluant: hexane/ethyl acetate (1:2)] to give 2.8 g of 1-di-n-propoxymethyl-2-nitroiminoimidazolidine.

SYNTHESIS EXAMPLE 12 (Intermediate No. 9)

22.0 g of methyl orthoformate was dropped in about 2 hours in a mixture of 10 g of 2-nitroiminoimidazolidine, 20 ml of 1,3-dimethyl-2-imidazolidinone and 0.05 g of sulfuric acid at 150° C., followed by heating under reflux for further 1 hour while removing the resultant distillate by means of the Dean-Stark trap. After cooling to room temperature, the mixture was poured into water, and extracted with ethyl acetate. After washing with water, the extract was dried with anhydrous magnesium sulfate, after which the solvent was distilled off under reduced pressure. The resultant crude crystals were sludged with ether to give 1.9 g of 1-dimethoxymethyl-2-nitroiminoimidazolidine.

SYNTHESIS EXAMPLE 13 (Intermediate No. 10)

20.0 g of methyl orthoformate was dropped in about 1.5 hours in a mixture of 10 g of 2-nitroiminohexahydropyrimidine, 20 ml of 1,3-dimethyl-2-imidazolidinone and 0.05 g of sulfuric acid at 150° C., followed by heating under reflux for further 1 hour while removing the resultant distillate by means of the Dean-Stark trap. After cooling to room temperature, the mixture was poured into water, and extracted with ethyl acetate. After washing with water, the extract was dried with anhydrous magnesium sulfate, after which the solvent was distilled off under reduced pressure. The resultant oily substance was purified by column chromatography [silica gel, eluant: hexane/ethyl acetate (1:2)] to give 1.5 g of 1-dimethoxymethyl-2-nitroiminohexahydropyrimidine.

SYNTHESIS EXAMPLE 14 (Intermediate No. 11)

A mixture of 10 g of 2-nitroiminohexahydropyrimidine, 12.4 g of ethyl orthoformate, 10 ml of 1,3-dimethyl-2-imidazolidinone was heated under reflux for 2.0 hours while removing the resultant distillate by means of the Dean-Stark trap. After cooling to room temperature, the mixture was poured into water, and extracted with ethyl acetate. After washing with water, the extract was dried with anhydrous magnesium sulfate, after which the solvent was distilled off under reduced pressure. The resultant oil was purified by column chromatography [silica gel, eluent: hexane/ethyl acetate (1:2)] to obtain 2.3 g of 1-diethoxymethyl-2-nitroiminohexahydropyrimidine. Typical examples of the compounds of the formula (2) which could be prepared according to the procedures similar to those of Examples 9 to 14 are shown in Table 3.

TABLE 3

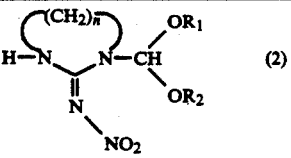

(2)

| Intermediate Compound No. | Substituents R₁ | R₂ | n | Values of Physical Properties |
|---|---|---|---|---|
| 1 | Et | Et | 2 | δTMS (CDCl₃) (ppm): 1.24(6H, t, J=6.9Hz), 3.44~3.87(8H, m), 5.95(1H, s), 8.36(1H, s) νMAX (KBr) (cm⁻¹): 3340, 1570, 1530, 1470, 1440, 1280, 1220, 1170, 1090, 1040 Elementary Analysis (C₈H₁₆N₄O₄): |

| | C | H | N |
|---|---|---|---|
| Calculated (%) | 41.37 | 6.94 | 24.13 |
| Found (%) | 40.94 | 6.90 | 24.58 |

TABLE 3-continued

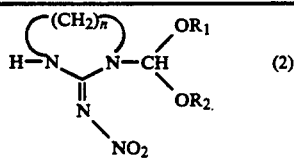

(2)

| Intermediate Compound No. | Substituents R₁ | R₂ | n | Values of Physical Properties |
|---|---|---|---|---|
| 2 | CH₃OC₂H₄ | CH₃OC₂H₄ | 2 | m.p.: 100.2~101.8° C.<br>δTMS (acetone-d₆) (ppm): 3.33(6H, s), 3.45~3.87(12H, m), 5.98(1H, s), 8.30(1H, broad-s)<br>νMAX (KBr) (cm⁻¹): 3375, 1575, 1447, 1108 |
| 3 | ClC₂H₄ | ClC₂H₄ | 2 | m.p.: 68.0~70.5° C.<br>δTMS (acetone-d₆) (ppm): 3.71~4.01(12H, m), 6.04(1H, s), 8.50~8.90(1H, broad-s)<br>νMAX (KBr) (cm⁻¹): 3359, 1574, 1443, 1290, 1098 |
| 4 | iso-Pr | iso-Pr | 2 | m.p.: 85.0~89.5° C.<br>δTMS (acetone-d₆) (ppm): 1.16~1.21(12H, m), 3.66~3.92(6H, m), 6.01(1H, s), 8.71(1H, broad-s)<br>νMAX (KBr) (cm⁻¹): 3423, 1565, 1433, 1283, 1083 |
| 5 | | CH₂CH₂ | 2 | m.p.: 137-146° C.<br>δTMS (acetone-d₆) (ppm): 3.55~4.10(8H, m), 6.49(1H, s), 8.08~8.45(1H, broad-s)<br>νMAX (KBr) (cm⁻¹): 3359, 1587, 1444, 1302, 1103 |
| 6 | nPr | nPr | 2 | m.p.: 123~126.5° C.<br>δTMS (CDCl₃) (ppm): 0.92~0.99(6H, m), 1.56~1.71(4H, m), 3.42~3.62(4H, m), 3.69~3.74(2H, m), 3.81~3.85(2H, m), 5.94(1H, s), 8.38(1H, broad-s)<br>νMAX (neat) (cm⁻¹): 3416, 1574, 1447, 1288, 1100 |
| 7 | CF₃CH₂ | Et | 2 | δTMS (acetone-d₆) (ppm): 1.23(3H, t, J=6.6Hz), 3.64~3.90(6H, m), 4.20(2H, q, J=8.8Hz), 6.06(1H, s), 8.84(1H, broad-s)<br>νMAX (KBr) (cm⁻¹): 3384, 1574, 1447, 1297, 1090 |
| 8 | CF₃CH₂ | Me | 2 | m.p.: 80~85° C.<br>δTMS (acetone-d₆) (ppm): 3.42(3H, s), 3.59~4.22(6H, m), 5.92(1H, s), 8.10~8.52(1H, broad-s)<br>νMAX (KBr) (cm⁻¹): 3397, 1582, 1444, 1286, 1110 |
| 9 | Me | Me | 2 | m.p.: 144° C. (dec.)<br>δTMS (CDCl₃) (ppm): 3.41(6H, s), 3.66~3.71(2H, m), 3.81~3.86(2H, m), 5.78(1H, s), 8.40(1H, broad-s)<br>νMAX (KBr) (cm⁻¹): 3367, 1577, 1533, 1289, 1104 |
| 10 | Me | Me | 3 | m.p.: 118~125° C.<br>δTMS (CDCl₃) (ppm): 2.04~2.09(2H, m), 3.40(6H, s), 3.45~3.70(4H, m), 6.28(1H, s), 9.80(1H, broad-s)<br>νMAX (KBr) (cm⁻¹): 3284, 1548, 1423, 1236, 1099 |
| 11 | Et | Et | 3 | δTMS (CDCl₃) (ppm): 1.23(6H, t, J=7.8Hz), 1.98~2.03(2H, m), 3.48(4H, q, J=7.8Hz), 3.51~3.57(2H, m), 3.64~3.70(2H, m), 6.50(1H, s), 9.98(1H, broad-s)<br>νMAX (KBr) (cm⁻¹): 3284, 1544, 1427, 1234, 1097<br>m.p.: 85.5~86.5° C. |

The compositions of the invention are more particularly described by way of Preparation Examples

FORMULATION EXAMPLE 1

20 parts by weight of the compound of the invention prepared in Synthesis Example 1, 10 parts by weight of Sorpol 355S (surfactant available from Toho Chem. Co., Ltd.) and 70 parts by weight of xylene were uniformly agitated and mixed to give an emulsifiable concentrate.

FORMULATION EXAMPLE 2

20 parts by weight of the compound of the invention prepared in Synthesis Example 1, 2 parts by weight of sodium alkylnaphthalenesulfonate, 5 parts by weight of sodium ligninsulfonate, 5 parts by weight of white carbon and 68 parts by weight of diatomaceous earth were uniformly agitated and mixed to give a wettable powder.

FORMULATION EXAMPLE 3

0.3 parts by weight of the compound of the invention prepared in Synthesis Example 1 was dissolved in acetone. While mixing with 99.7 parts by weight of clay, the acetone was evaporated to give a powder.

FORMULATION EXAMPLE 4

2 parts by weight of the compound of the invention prepared in Synthesis Example 1, 2 parts by weight of sodium ligninsulfonate, and 96 parts by weight of bentonite were uniformly divided into pieces and mixed, to which water was added for kneading, followed by granulation and drying to give a granular.

The insecticidal activity of the compounds of the formula (1) is particularly by way of test examples.

TEST EXAMPLE 1

Effect on *Laodelphax striatellus* Fallen—Smaller Brown Planthopper

The emulsion prepared in Formulation Example 1 was diluted to predetermined concentrations and 2 ml of each diluted emulsion was applied over a bundle of several rice seedlings (about third leaf stage). After drying in air, the treated seedlings were covered with a metal gauze cylinder, in which ten female adults of the smaller brown planthopper were released, followed by placing in a temperature controlled room at 25° C. After 48 hours, the mortality was checked. The results are shown in Table 4. For a control chemical, there was used the compound as shown below.

TABLE 4

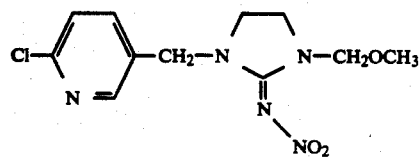

| Test Compound No. | Mortality (%) | |
|---|---|---|
| | 100 ppm | 10 ppm |
| No. 1 | 100 | 100 |
| No. 2 | 100 | 100 |
| No. 3 | 100 | 100 |
| No. 4 | 100 | 100 |
| No. 5 | 100 | 95 |
| No. 6 | 100 | 100 |
| No. 7 | 100 | 100 |
| No. 8 | 100 | 90 |
| No. 9 | 100 | 100 |
| No. 10 | 100 | 100 |
| No. 11 | 100 | 100 |
| Reference Compound | 30 | 0 |
| Non treated | 0 | 0 |

TEST EXAMPLE 2

Effect on Resistant Strain of *Nephotettix cincticepts* Uhler—Resistant Gree Rice Leafhopper The emulsion prepared in Formulation Example 1 was diluted to predetermined concentrations and each solution was applied in an amount of 3 ml over a bundle of several rice seedlings (about third lead stage). After drying in air, the treated seedlings were covered with a metal gauze cylinder, in which ten female adults of leafhopper that is resistant to organophosphate and carbamate agents were released, followed by placing in a temperature controlled room. After 48 hours, the mortality was checked. The results are shown in Table 5. For a control chemical, there was used the same compound in Test Example 1.

TABLE 5

| Test Compound No. | Mortality (%) | |
|---|---|---|
| | 10 ppm | 1 ppm |
| No. 1 | 100 | 100 |
| No. 2 | 100 | 100 |
| No. 3 | 100 | 100 |
| No. 4 | 100 | 100 |
| No. 5 | 100 | 100 |
| No. 6 | 100 | 90 |
| No. 7 | 100 | 100 |
| No. 8 | 100 | 100 |
| No. 9 | 100 | 100 |
| No. 10 | 100 | 100 |
| No. 11 | 100 | 100 |
| Reference Compound | 100 | 45 |
| Non treated | 0 | 0 |

TEST EXAMPLE 3

Effect on *Callosobruchus chinensis* Linne—Azuki Bean Weevil

An acetone solution of the compound of the invention prepared in Synthesis Example 1 was added to Petri dish with a diameter of 9 cm, followed by removal of the acetone by evaporation. Twenty female adults of the Azuki bean weevil, which were 2 to 3 days after emergence were placed in the dish at 25° C. After 48 hours, the mortality was checked. The results are shown in Table 6. For a control chemical, there was used diazinon of the formula (7) [O,O-diethyl O-(2-isopropyl-6-methyl-4-pyrimidinyl)phosphorothioate].

TABLE 6

| Test Compound No. | Mortality (%) | |
|---|---|---|
| | 0.1 mg/dish | 0.001 mg/dish |
| No. 1 | 100 | 100 |
| Diazinone | 95 | 30 |
| Non treated | 2.5 | |

TEST EXAMPLE 4

Effect on *Myzus persicae* Sulzer—Green Peach Aphid

Dilutions of the emulsifiable concentrate prepared in Formulation Example 1 were sprayed in an amount of 20 ml over potted eggplant seedlings (fourth or fifth leaf stage) on which the gree peach aphid had been parasitic. After the application, the seedlings were placed in a greenhouse and, after three days, the number of the aphids were checked. The results are shown in Table 7. For a control chemical, there was used the same compound in Test Example 1.

TABLE 7

| Test Compound No. | Number of Parasitic aphids Concentration (1 ppm) | |
|---|---|---|
| | Prior to Treatment | After Three Days |
| No. 1 | 125 | 0 |
| No. 2 | 98 | 0 |
| No. 3 | 111 | 0 |
| No. 4 | 106 | 0 |
| No. 5 | 132 | 0 |
| No. 6 | 89 | 0 |
| No. 7 | 94 | 0 |
| No. 8 | 131 | 0 |
| No. 9 | 105 | 0 |
| Reference Compound | 120 | 92 |
| Non treated | 103 | 146 |

As will be apparent from the foregoing description, the imidazolidine derivatives of the formula (1) according to the invention have high insecticidal efficacy and a wide insecticidal spectrum. The imidazolidine derivatives of the formula (1) can be readily prepared according to a process of the invention using novel intermediates of the formula (2). The agricultural chemicals comprising the imidazolidine derivatives of the formula (1) have good characteristics as an insecticide.

We claim:

1. An imidazolidine of the formula (1)

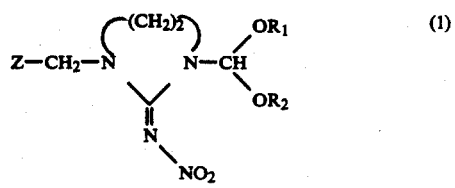

wherein Z represents a 2-chloropyridin-5-yl group or a 2-chlorothiazol-5-yl group, $R_1$ and $R_2$, respectively, represent a lower alkyl group having from 1 to 6 carbon atoms, a lower haloalkyl group having from 1 to 3 carbon atoms or a lower alkyl group having from 1 to 3 carbon atoms and substituted with a lower alkoxy group having from 1 to 3 carbon atoms, or $R_1$ and $R_2$ are joined to form a cyclic alkylene group having from 2 to 3 carbon atoms.

2. An imidazolidine according to claim 1, wherein, in the formula (1), $R_1$ and $R_2$ are independently a lower alkyl group having from 1 to 4 carbon atoms and Z is a 2-chloropyridin-5-yl group.

3. An insecticidal composition comprising, in admixture with a carrier, an insecticidally effective amount of a compound of claim 1.

4. An insecticidal composition according to claim 3, wherein, in formula (1), $R_1$ and $R_2$ are independently a lower alkyl group having from 1 to 4 carbon atoms and Z is a 2-chloropyridin-5-yl group.

* * * * *